United States Patent [19]

Herrero-Vanrell et al.

[11] Patent Number: 5,718,922
[45] Date of Patent: Feb. 17, 1998

[54] INTRAVITREAL MICROSPHERE DRUG DELIVERY AND METHOD OF PREPARATION

[75] Inventors: Rocio Herrero-Vanrell, Madrid, Spain; Miguel F. Refojo, Wellesley, Mass.

[73] Assignee: Schepens Eye Research Institute, Inc., Boston, Mass.

[21] Appl. No.: 455,091

[22] Filed: May 31, 1995

[51] Int. Cl.$^6$ .............................. A61K 9/50; A61K 9/16; B32B 5/16; B01J 13/02
[52] U.S. Cl. .............................. 424/501; 424/490; 424/497; 428/402; 264/4.1; 264/4.3; 264/4.33; 264/4.6
[58] Field of Search .............................. 424/489, 490, 424/497, 501; 428/402; 264/4.1, 4.3, 4.33, 4.6

[56] References Cited

U.S. PATENT DOCUMENTS

| | | | |
|---|---|---|---|
| 5,049,322 | 9/1991 | Devissaguet et al. | 264/4.1 |
| 5,118,528 | 6/1992 | Fessi et al. | 427/213.36 |
| 5,288,502 | 2/1994 | McGinity et al. | 424/484 |
| 5,384,333 | 1/1995 | Davis et al. | 514/772.3 |

OTHER PUBLICATIONS

Alonso, M.J. et al. (1993) "Determinants of Release Rate of Tetanus Vaccine from Polyester Microspheres" Pharmaceutical Research 10(7):945–953.

Bodmeier, R. and J.W. McGinity (1988) "Solvent Selection in the preparation of poly(DL–lactide) microspheres prepared by solvent evaporation method" International Journal of Pharmaceutics 43:179–186.

Buchi, E.R. (1988) "Long–Term Intravitreal Ganciclovir for Cytomegalovirus Retinitis in a Patient with AIDS" Arch. Ophthalmol. 106:1349–1350.

Cantrill, H. L. et al. (1989) "Treatment of Cytomegalovirus Retinitis with Intravitreal Ganciclovir. Long term results" Ophthalmology 96(3):367–374.

Chen, S. (1992) "Xanthomonas Maltophilia Endophthalmitis After Implantation of Sustained–Release Ganciclovir" American J. of Ophthalmology 114(6):772–773.

Chisp, P. and S.P. Clissold (1991) "Foscarnet. A Review of its Antiviral Activity, Pharmacokinetic Properties and Therapeutic Use In Immunocompromised Patients with Cytomegalovirus Retinitis" Drugs 41(1):104–129.

Cohen, S. et al. (1991) "Controlled Delivery Systems for Proteins Based on Poly(lactic/glycolic Acid) Microspheres" Pharmaceutical Research 8(6):713–720.

(List continued on next page.)

Primary Examiner—Carlos A. Azpuru
Attorney, Agent, or Firm—Lahive & Cockfield, LLP

[57] ABSTRACT

A method of forming microspheres containing a hydrophilic drug or agent for injection to provide localized treatment over a protracted time with sustained delivery in a therapeutically indicated rate band. The drug or agent is first dispersed or suspended as a micropulverized solid in an inert hydrophobic oil and sonicated with a non-aqueous solution of a biodegradable polymer. The dispersion is then stabilized in a second oil to remove solvent from the microspheres. Non-aqueous solvents are used throughout, and high drug concentrations are obtained simultaneously with enhanced control over a uniform and sustained delivery rate with extended duration of delivery. In vitro studies of ganciclovir in a silicone oil/fluorosilicone oil/PLGA system yield microsphere fractions that provide dose levels in a therapeutic range for CMV retinitis from only a single intravitreal injection that lasts substantially in excess of one month. The preparation method allows drug loading efficiencies above ninety percent. By protecting the drug in an inner phase carrier of biocompatible but not biodegradable oil, and forming biodegradable shells and pore-defining foliations within the microspheres, the rate of control of solvent erosion pathways into the microspheres is extended, and selection of the polymer and of the oils allow control over both the delivery rate and time.

18 Claims, 5 Drawing Sheets

OTHER PUBLICATIONS

Cumming, J.S. (1980) In Ophthalmic Drug delivery systems (Chapter 1—Relevant Anatomy and Physiology of Eye) Robinson, J.R., Ed; American Pharmaceutical Association, Washington D.C. pp. 1–27.

Faulds, D. and R.C. Heel (1990) "Ganciclovir A Review of its Antivity, Pharmocokinetic Properties and Therapeutic Efficacy in Cytomegalovirus Infections" Drugs 39(4):597–638.

Freeman, W.R. (1989) "Intraocular Antiviral Therapy" Arch. Ophthalmol. 107:1737–1739.

Gliding, D.K. Biocompat. (Chapter 9—"Biodegradable Polymers") Implant. Mater. 2:209–232.

Giordano, G.G. (1993) "Sustained Delivery of Retinoic Acid From Microspheres of Biodegradable Polymer in PVR" Investigative Ophthalmology & Visual Science 34(9):2743–2451.

Heinemann, et al. (1989) "Long–Term Intravitreal Ganciclovir Therapy for Cytomegalovirus Retinopathy" Arch. Ophthalmol. 107:1767–1772.

Henderly, D.E. (1987) "Cytomegalovirus Retinitis and Response to Therapy with Ganciclovir" Ophthalmology 94(4):425–434 and correspondence related thereto in 103(6):842–843.

Henry, K. et al. (1987) "Use of Intravitreal Ganciclovir (Dihydroxy Propoxymethyl Guanine) for Cytomegalovirus Retinitis in a Patient with AIDS" American J. of Ophthalmology 103(1):17–23.

Holland, G.N. et al. (1986) "Treatment of Cytomegalovirus Retinopathy in Patients with Acquired Immunodeficiency Syndrome" Arch. Ophthalmol. 104:1794–1800.

Holland, G. N. et al. (1989) "A Controlled Retorspective Study of Ganciclovir Treatment for Cytomegalovirus Retinopathy" Arch Ophthalmol. 107:1759–1766.

Holland, G. N. (1987) "Treatment of Cytomegalovirus Retinopathy with Ganciclovir" Ophithalmology 94(7):815–823.

Iwata, Motokazu and J.W. McGinity (1993) "Dissolution, Stability, and Morphological Properties of Conventional and Multiphase Poly (DL–Lactic–Co Glycolic Acid) Microspheres Containing Water–Soluble Compounds" Pharmaceutical Research 10(8):1219–1229.

Jabs, D.A. et al. (1989) "Cytomegalovirus Retinitis and Acquired Immunodeficiency Syndrome" Arch. Ophthalmol. 107:75–80.

Jalil, R. and J.R. Nixon (1990) "Biodegradable poly(lactic acid) and poly(lactide–co–glycolide) microcapsules: problems associated with preparative techniques and release properties" J. Microencapsulation 7(3):297–325.

Martin, D.F. (1994) "Treatment of Cytomegalovirus Retinitis With an Intraocular Sustained–Release ganciclovir Implant" Arch Ophthalmol. 112:1531–1539.

Miyamoto, K. et al. (1986) "Fluorinated Oils as Experimental Vitreous Substitutes" Arch. Ophthalmol. 104:1053–1056.

Moritera, T. (1991) "Microspheres of Biodegradable Polymers as a Drug–Delivery System in the Vitreous" Investigative Ophthalmology & Visual Science 32(6):1785–1790.

Orellana, J. (1987) "Combined Short– and Long –term Therapy for the Treatment of Cytomegalovirus Retinitis Using Ganciclovir (BW B759U)" Ophthalmology 94(7):831–838.

Robinson, M.R. et al. (1986) "Treatment of Cytomegalovirus Optic Neuritis with Dihydroxy Propoxymethyl Propoxymethyl Guanine" 102(4):533–534.

Sanborn, G.E. (1992) "Sustained–Release Ganciclovir Therapy for Treatment of Cytomegalovirus Retinitis. Use of an Intravitreal Device" Arch. Ophthalmol. 110:188–195.

Sidikaro, Y. (1991) "Rhegmatogenous Retinal Detachments in Patients with AIDS and Necrotizing Retinal Infections" Ophthalomology 98(2):129–135.

Smith, J.T. (1992) "Intravitreal Sustained–Release Ganciclovir" Arc. Ophthalmol 110:255–258.

Tolentino, F.I. (1988) In Proliferative Vitreoretinopathy (PVR); Freedman, H.M.; Tolentino, F.I. Eds. Springer–Verlag, New York "High–Density Fluorosilicone Oil in Vitreous Surgery" pp. 177–180.

Ussery, F.M. (1988) "Intravitreal Ganciclovir in the Treatment of AIDS–associated Cytomegalovirus Retinitis" Ophthalmology 95(5):640–648.

INTRAVITREAL MICROSPHERE DRUG DELIVERY AND METHOD OF PREPARATION

BACKGROUND

The present invention relates to methods of preparing encapsulated drugs or drug microspheres for localized delivery, and to the microspheres so obtained. It also relates to treatment of disease or local infection.

A great number of techniques exist for loading drugs into protective matrices or shells to protect a pharmacological agent from its environment or control its rate of delivery. Such techniques, in theory, may be used to prepare a range of particle sizes, from nanoparticles, as described in U.S. Pat. Nos. 5,118,528 and 5,049,322, to microspheres. In general, these systems involve dispersions or emulsions in which the drug is initially loaded in one of the phases, and the emulsion or dispersion is subsequently dried or hardened, with the drug captured in precipitated matrix or encased droplets to form microspheres. The amount of drug loading, and the subsequent drug release properties both depend on the specific materials and techniques used, and even small improvements in either of these properties can substantially affect the efficacy or economics of drug manufacture or administration.

Up to the present, a number of clinical uses of encapsulated agents have been proposed, from holding culture material within a porous barrier in an implanted organ, to intravenous injection of the particles to enable them to reach a target site by navigating through blood vessels, to injection of such microcapsules directly into an affected organ, e.g., the eyeball as shown in U.S. Pat. Nos. 4,853,224 and 4,997,657. However, because of the special circumstances prevailing at each site, any of these described techniques may require a substantial amount of work or basic research in order for a particular active agent to reach effective implementation. A good survey of drug encapsulation approaches and the problems to be overcome may be found in U.S. Pat. No. 5,288,502. That patent is hereby incorporated herein by reference for its teachings.

Recently, there has been a high incidence of cytomegalovirus (CMV) retinitis, which might benefit from the development of new treatment methods and delivery system. Existing treatments used powerful drugs (ganciclovir and foscarnet) which must be administered in controlled doses and preferably with limited systemic concentrations. However, drug treatment of this disease is problematic.

Cytomegalovirus (CMV) retinitis is an ocular infection that occurs frequently in acquired immune deficiency syndrome (AIDS). Without treatment, the infection is progressive and results in blindness from retinal detachment associated with retinal necrosis. Ganciclovir and foscarnet are the only available drugs that effectively treat CMV retinitis. In most-cases an intravenous dose of 10 mg/Kg daily, for 7 to 21 days of ganciclovir effectively halts disease progression. Unfortunately, the disease recurs after discontinuation of the drug. Even on a maintenance therapy of 5 mg/Kg daily, for 5 days/week, CMV recurs in 30 to 50% of patients. Dose-dependent myelosuppression prevents maintenance therapy in about 15% of patients. Myelosuppression also necessitates that patients on maintenance ganciclovir discontinue zidovudine, a drug used to treat human immunodeficiency virus. Sepsis related to permanent indwelling catheters is another problem associated with systemic ganciclovir administration.

Intravitreal ganciclovir injections provide higher intraocular drug concentrations than systemic therapy and reduce systemic concentrations. However, the intravitreal half-life of ganciclovir, estimated to be approximately 13 hours, requires frequent injections (1 to 3 times/week) to maintain therapeutic ocular levels. Intravitreal ganciclovir injections of 200 to 400 μg administered weekly produce temporary remission of CMV retinitis. However, repeated intravitreal injections are poorly tolerated and are associated with cataract formation, retinal detachment, cystoid macular edema, and endophthalmitis.

In vitro studies have indicated that the median concentration of ganciclovir required for 50% inhibition of CMV replication (ED50) is between 0.02 and 3.48 μg/ml. The short intravitreal half-life of ganciclovir and its systemic toxicity make the drug a good candidate for use in a local sustained delivery system. Such intravitreal therapy does not produce significant systemic drug levels, thus allowing concurrent administration of systemic zidovudine. One intraocular nonbiodegradable sustained delivery device is available, in the form of an implant in sizes that maintain therapeutic levels of ganciclovir for periods of 42 or 226 days. However, ocular implantation of this device may cause vitreous hemorrhage and retinal detachment, and surgical removed of the spent device is required. It has also been proposed in U.S. Pat. No. 5,384,333 to compound the drug with a meltable polymer that can be injected and cooled in situ to provide a sustained release body in the eye. However, applicant is not aware of any accepted implementation of this treatment approach.

Accordingly, it would be desirable to develop microspheres of biodegradable polymer loaded with ganciclovir that are capable of providing a sustained-release delivery rate of the drug with a single intravitreous injection.

More generally, it would be desirable to develop microspheres for local delivery of a hydrophilic treatment agent, wherein the microspheres have a size distribution that allows direct injection, yet carry the agent so highly blocked from dissolution in an aqueous environment that the microspheres possess extended and uniform in vivo release characteristics.

SUMMARY OF INVENTION

These and other desirable traits are obtained in a microsphere treatment protocol wherein the microspheres are formed in a polymer/oil dispersion with a hydrophilic drug suspended in the oil phase. The oil substantially prevents partition during microsphere formation, and results in high drug loading. The polymer/oil drug dispersion is dispersed in a second incompatible oil containing an emulgent. With this mixture stirring under evaporative conditions, the microspheres precipitate out and dry holding the drug protected within a body formed of an external polymer shell and inner striae and lacunae. The first oil essentially renders the drug hydrophobic, and by using non-aqueous solvents, re-partition or solution of the drug is avoided during all the steps of microsphere formation, resulting in microspheres with a high drug loading and highly hindered solution or biodegradation characteristics.

In an exemplary embodiment, a mixture of ganciclovir suspended in a fluorosilicone oil is mixed with solution of poly(lactide-co-glycoside) (PLGA) in acetone to form a dispersion, which is then emulsified in an excess of acetone-silicone oil containing the emulgent to produce the microspheres. The two oils are immiscible, and are biocompatible but non-biodegradable, although in other embodiments, one or both of the oils may be replaced by biodegradable oils having appropriate viscosity, solvation and immiscibility to achieve such release characteristics. For example, (±)α- tocopherol or a corresponding acetate may be used as a biodegradable oil. For intravitreal delivery, the microcapsules are prepared at a loading over 80%, and preferably over 90% loading. They are then graded for size, with a specific range of diameters being selected to achieve a stable release profile in excess of one month when delivered in vivo.

In one particularly preferred aspect of the present invention, a suspension of a water-soluble powdered active agent or compound in a fluorosilicone oil is dispersed in a greater volume of a non-aqueous solution of a hardenable biodegradable polymer. This dispersion or emulsion has as its continuous phase the hardenable polymer, while the active compound resides almost entirely in the discontinuous phase fluorosilicone oil. The dispersion is then mixed in a similar volume of a second oil/solvent. The solvent used for the polymer is partially soluble in the second oil, and the dispersion is further performed with an emulsifier, enhancing the phases separation in the second oil. The combined oil/polymer/oil preparation is then stirred in a much greater volume of the second oil/solvent under evaporative conditions to extract the solvent. This solvent extraction in oil and evaporation from the oil hardens the polymer which forms a spherical shell enclosing the compound within lacunae of the fluorosilicone oil that are further encased or compartmentalized by inner striae and walls formed of the hardened or hardening PLGA polymer. All solvents are non-aqueous and the oils are mutually immiscible, so the compound remains in the fluorosilicone oil phase throughout preparation and hardening, yielding drug loadings of 80–95% or more.

In a CMV retinitis treatment protocol, the drug-oil is encapsulated in a matrix of biodegradable polymer formed as microspheres that are directly injected into a patient's vitreous humor in a single dose and provide a sustained rate that maintains a therapeutic level of the drug in the vitreous.

BRIEF DESCRIPTION OF THE DRAWINGS

These and other features of the invention will be understood from the description herein taken together with illustrative figures, wherein.

DETAILED DESCRIPTION

Poly(DL-lactide-co-glycolide) [PLGA] microspheres were selected as a potential vehicle for intraocular ganciclovir therapy. Extensive experience has shown that this polymer is biocompatible and degrades to metabolic products that are eliminated from the body.

With this matrix carrier, a number of experiments were undertaken to determine if a hydrophilic drug, ganciclovir sodium salt, could be encapsulated in a manner to provide sustained drug release in the vitreous. Closely related results are expected for foscarnet and other hydrophilic agents, and for such agents which may be prepared as finely divided powders.

Experimental Section

Materials: Ganciclovir sodium salt (BW B759 U, DHPG, dihydroxy propoxymethyl guanine) was obtained from Syntex Laboratories (Palo Alto, Calif.). Poly(DL-lactide-coglycolide) [PLGA] with a 50/50 ratio of DL-lactic to glycolic acids and inherent viscosity of 0.53 dl/g in chloroform was obtained from Medisorb Technologies International. (Stolle Dupont Company, Cincinnati, Ohio) and PLGA with inherent viscosities 0.65, 0.42, and 0.39 dl/g in hexafluoroisopropanol were purchased from Birmingham Polymers Inc. (Birmingham, Ala.). The ranges of the molecular weight corresponding to the inherent viscosities of the polymers are the following: 0.65 dl/g: 15,000–18,000 daltons; 0.53 dl/g: 12,000–15,000 daltons; and 0.42, and 0.39 dl/g: 9,000–12,000 daltons. Polyvinyl alcohol (PVA) of 78,000 daltons, 88% hydrolyzed, was obtained from Polysciences Inc. (Warrington, Pa.). Methylene chloride, hexane and N,N-dimethyl formamide were purchased from Fisher Scientific (Pittsburgh, Pa.). Castor oil was obtained from Aldrich Chemical Company (Milwaukee, Wis.). Silicone oil (SiO, polydimethylsiloxane, trimethylsiloxy terminated ) with a viscosity of 500 centistokes (cs), fluorosilicone oil (FSiO, polymethyl - 3,3,3-trifluoropropyl siloxane) with a viscosity of 1000 cs, and dimethylsiloxane ethylene oxide - propylene oxide copolymer (DMSiEPO) with a viscosity of 1800 cs, were obtained from Hüls America Inc. (Piscataway, N.J.). Sesame oil and soybean lecithin were from Sigma Chemical (St. Louis, Mo.), and the emulgent sold under the trademark Pluronic P84 was obtained from BASF Corporation (Parsippany, N.J.).

Methods:

Applicants evaluated three techniques to prepare PLGA/ganciclovir microspheres, which are referred to as technique 1, technique 2 and technique 3 below. Techniques 1 and 2 have been reported before for other drug preparations. However, they were found to be unsuitable.

Technique 1:

The preparation was based on the solvent evaporation method using a double emulsion technique as reported by S. Cohen et al. in Pharm. Res. 1991, 8,713–720. Briefly, an amount of ganciclovir sodium salt equivalent to 5, 10, 20, or 30 mg of free ganciclovir was dissolved in 25, 50, 75, or 100 µl of phosphate buffer pH 11, or in distilled water, and poured into a solution of 0.5 grams of PLGA (0.65, 0.53, or 0.42 dl/g, respectively) in 0.5 ml methylene chloride. The mixture was stirred for one or two minutes in a vortex mixer (Vortex-Genie, Scientific Industries Inc., Springfield, Mass.) at maximum speed to form a first, inner emulsion (W1/O). One ml of aqueous 1% PVA saturated with methylene chloride was added under vigorous mixing (vortex) for 10 seconds to form a second emulsion (W1/O/W2). The resulting double emulsion was poured into the stirred external aqueous phase (100 ml 0.1% PVA) and left on the magnetic stirrer for three hours at room temperature, in the hood, until the methylene chloride evaporated leaving solid microspheres. After rinsing three times with distilled water, the microspheres were collected by centrifugation, sieved into various particle size fractions (300, 212,106, and 53 µm), and freeze-dried for twenty hours. The dried microspheres were stored under reduced pressure over anhydrous $CaSO_4$ until they were assayed.

Technique 2:

This method also was based on the solvent evaporation method, with the exception that an oil was used as the external phase of the emulsion instead of aqueous PVA, as reported by T. Moritera et at. Invest. Ophthalmol. Vis. Sci. 1991, 32, 1785–1790. Ganciclovir sodium salt (equivalent to 50 mg of ganciclovir) and 450 mg of PLGA (0.65 or 0.53 dl/g) was dissolved in 5 ml of N,N-dimethyl formamide. This solution was then emulsified in 100 ml of castor oil, sesame oil, or SiO containing an emulgent soybean lecithin (50 mg), Pluronic P84 (50 mg), or DMSiEPO (200 µl), respectively. The oil-in-oil emulsion was stirred at 45 °C. for twenty-four hours under the hood until most of the dimethyl formamide evaporated.

Technique 3:

A solution of 250 mg PLGA in acetone (in one ml for the 0.53 dl/g PLGA, and in 1.0 ml, 0.8 ml or 0.7 ml for the 0.42 and 0.39 dl/g PLGA, respectively) was added to a mixture of ganciclovir sodium (equivalent to 25 mg or 12.5 mg free ganciclovir, respectively) in FSiO (100 µl ) and the suspension was agitated in vortex for 1 min and sonicated (50 Sonic Dismembrator, Fisher Scientific) for 5 minutes at high speed, using intervals of one minute of sonication and ten seconds of resting period between sonications. The polymer-FSiO-ganciclovir-mixture was added to 2 ml of a solution of 50 ml SiO, 5 ml of acetone, and 100 µl DMSiEPO emulgent, and then was sonicated again for 25 seconds at high speed (#18, outpower 80%) to create a two-oil dispersion in acetone/emulgent. This dispersion then was added to the remaining SiO-acetone-emulgent solution and stirred overnight in the hood, at room temperature, until the acetone evaporated leaving solid microspheres. The microspheres were washed twice with hexane, separated using different sieves (300, 212, 106, 53 and 38 µm), and dried over anhydrous $CaSO_4$ in a vacuum desiccator for at least 48 hours. They were then subjected to in vitro drug release assays.

Ganciclovir Concentration in the Microspheres

Duplicate samples of microspheres were accurately weighed (10 mg) and dissolved in 2 ml methylene chloride. The ganciclovir was extracted from the methylene chloride twice into 3 ml of distilled water. The amount of drug was measured spectrophotometrically at absorbance 250.5 nm (Beckman DU-70 Spectrophotometer. Fullerton, Calif.).

Microsphere Morphology

Microsphere samples were observed by light microscopy. The morphology of the microspheres before and at different stages of the release assays was determined by scanning electron microscopy (SEM) (AMR Model A). The samples were dried and gold sputter-coated before observation by SEM at 20 Kv with a 12 mm working distance.

Ganciclovir Release Studies

For each of the preparation techniques described above, duplicate 10 mg samples of microspheres were suspended in 1.5 ml 0.01M phosphate buffer solution pH 7.0 (PBS), and placed in a shaker at room temperature (Mistrat Multi-Mixer, Lab-Line Instruments Inc., Melrose Park; Ill.). Periodically, the PBS was removed with a syringe, filtered through a 0.45-µm filter (Gelman, Acrodisc LC 13 PVDF), and analyzed for ganciclovir by monitoring its absorbance at 250.5 nm. The same amount of fresh PBS was added to the microspheres to continue the release study.

When the release assay was concluded, the microspheres were dried for two days in a desiccator under vacuum, and the residual ganciclovir was then extracted from the polymer and analyzed as described above.

Results

The microspheres formed by technique 1 were spherical and did not aggregate. Microspheres entrapped different amounts of ganciclovir depending on the quantity of initial drug and the amount of solvent used to dissolve the drug (internal phase of the first emulsion). Initially, the solvents used were buffer pH 11 and distilled water. Similar results were obtained for both solvents, so distilled water was used in most preparations. When solid ganciclovir sodium was added to the polymer-methylene chloride solution, the drug entrapment in the microspheres was negligible.

When the amount of drug in the preparation was increased, the drug loading in the microspheres decreased. In addition, for a given amount of drug, increasing the volume of water to dissolve the drug decreased the amount of drug entrappeal in the microspheres. The best results for drug loading by this technique amounting to about 60% of theoretical drug content, were obtained with the 0.65 dl/g polymer in the 212 µm microspheres, using 10 mg of free ganciclovir dissolved in 25 µl of water. The drug loading was lower in the smaller microspheres (45% in the 106-µm fraction, and 40% in the 53 µm fraction). The other, lighter polymer fractions tested always entrapped less than 50% of the initial ganciclovir for all the microsphere sizes.

The distribution of microsphere sizes depended on the mixing rate of the second emulsion and the molecular weight of the polymer. Prepared under the same working conditions, the 15,000–18,000 dalton polymer with a higher inherent viscosity (0.65 dl/g) yielded a major fraction of microspheres with diameters ranging from 53–212 µm. The polymers with lower inherent viscosities (0.53 and 0.42 dl/g) yielded major fractions of microspheres ranging from 38 to 106 µm.

Figure 1:
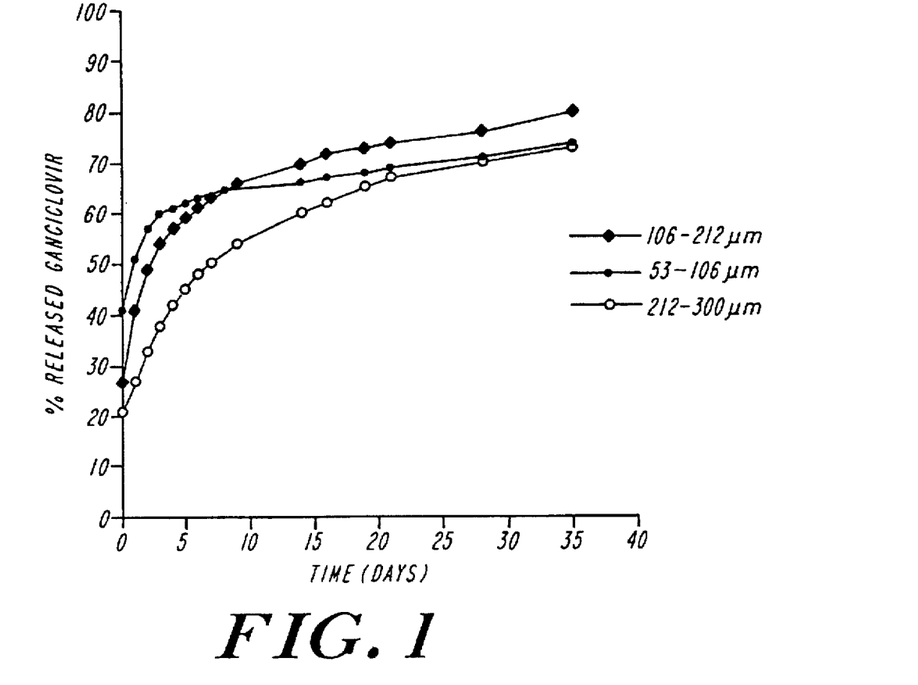
FIG. 1 shows in vitro drug release curves of microspheres prepared by a prior art technique.

The ganciclovir delivery in the assay depended on the molecular weight of the polymer and the microsphere sizes. In all the batches prepared by this technique, with the exception of the 0.65 dl/g polymer, the release profile was characterized by an initial ganciclovir burst of more than 50% of the drug loading for the 53–106 µm microspheres during the first day, followed by a rapidly decreasing rate of drug release during the following 10 days. Thereafter, less drug was released for at least 35 days. However, in all cases, independently of the molecular weight of the polymer, the amounts of ganciclovir released from 10 mg of microspheres during the assay were too low. In all cases, the larger microspheres (212–300 µm) released ganciclovir at a slower rate than the smaller (53–106 µm) microspheres. Although microspheres prepared from the 0.65 dl/g polymer produced an initial burst that was slightly lower than the other polymers, the amounts of ganciclovir released were too deemed to be low compared with the concentrations obtained with the existing ganciclovir implant delivery system. The ganciclovir release curves from the 53–106, 106–212, and 212–300 µm microspheres prepared according to technique 1 are shown in FIG. 1.

In all experiments performed using technique 2, most of the polymer precipitated and only small amounts of aggregated microspheres formed. The prospects of being able to provide an effective formulation seemed poor. Therefore, no ganciclovir release assays were performed for the microspheres formed by technique 2 of the prior art.

For technique 3, the method of the present invention, polymers with inherent viscosities of 0.53 dl/g, 0.42 dl/g, and 0.39 dl/g, and polymer/drug ratios of 250 mg/12.5 mg and 250 mg/25 mg were used. Each formulation formed well-shaped microspheres, which were sieved into 53–106, 106–212, 212–300, and 300–500 μm diameter fractions. Drug loading was exceptionally high. The percentage of ganciclovir per theoretical ganciclovir in the microspheres was 90–95% in all cases for the large microspheres (212–300 μm and 300–500 μm), and somewhat lower for the smaller diameter fractions.

The solutions of 0.42 dl/g and 0.39 dl/g PLGA in 0.8–1.0 ml acetone had relatively lower viscosity and yielded less rounded microspheres with lower ganciclovir loading than the same polymers dissolved in 0.7 ml acetone. No marked differences were found between the results obtained with 0.42 dl/g or 0.39 dl/g polymer dissolved in 0.7 ml of acetone. Microspheres prepared from 0.39 dl/g polymer released the drug slightly faster than those prepared with 0.42 dl/g polymer.

Comparison to the Prior Art Microsphere Preparation Technique

Figure 2:
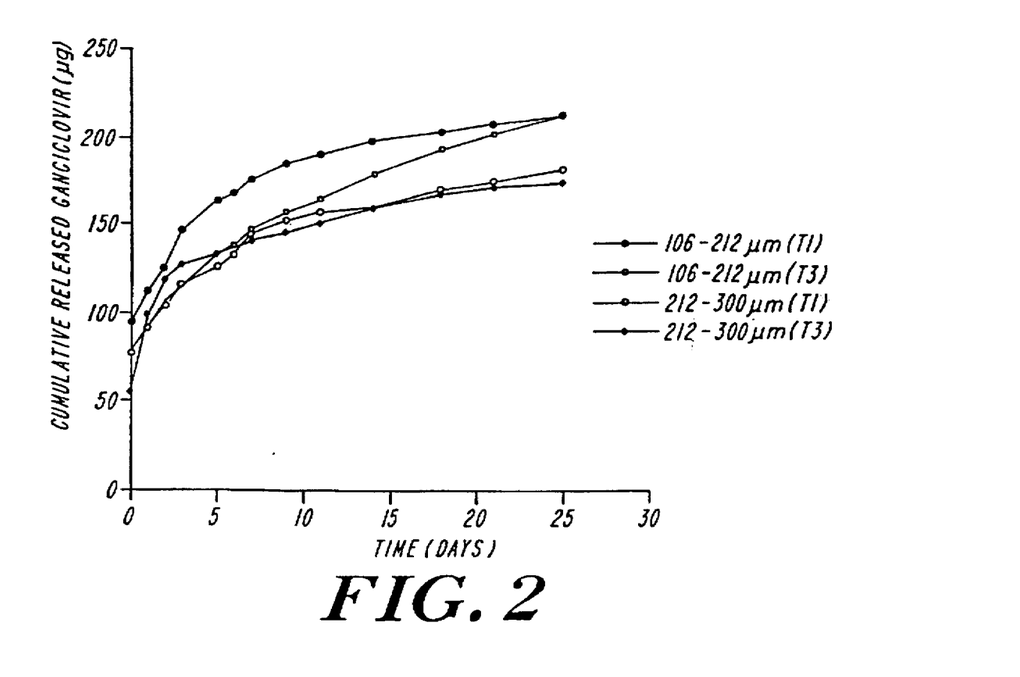
FIG. 2 shows comparative drug release of microspheres prepared by the prior art and prepared in accordance with the present invention.

We compared the ganciclovir loading and release from the 0.53 dl/g polymer microspheres obtained by the prior art technique 1 using 25 mg ganciclovir in 25 μl water and 500 mg polymer, and microsphere prepared in accordance with the present invention by technique 3 using 12.5 mg ganciclovir in 100 μl FSiO, and 250 mg polymer in 1 ml acetone, respectively. The technique 1 microspheres encapsulated only 51% of the drug in the 212–300 μm and 42% in the 106–212 μm microspheres. In comparison, the technique 3 microspheres of the present invention encapsulated 97% of the drug in the 212–300 μm and 91% of the drug in the 106–212 μm microspheres. The technique 3 microspheres consistently delivered more ganciclovir daily than those made by technique 1. By day twenty-five, the 106–212 μm technique 1 microspheres had released about 90% of the drug; the same size microspheres in accordance with the present invention had delivered less than 50% of the encapsulated drug (FIG. 2).

Figure 3:
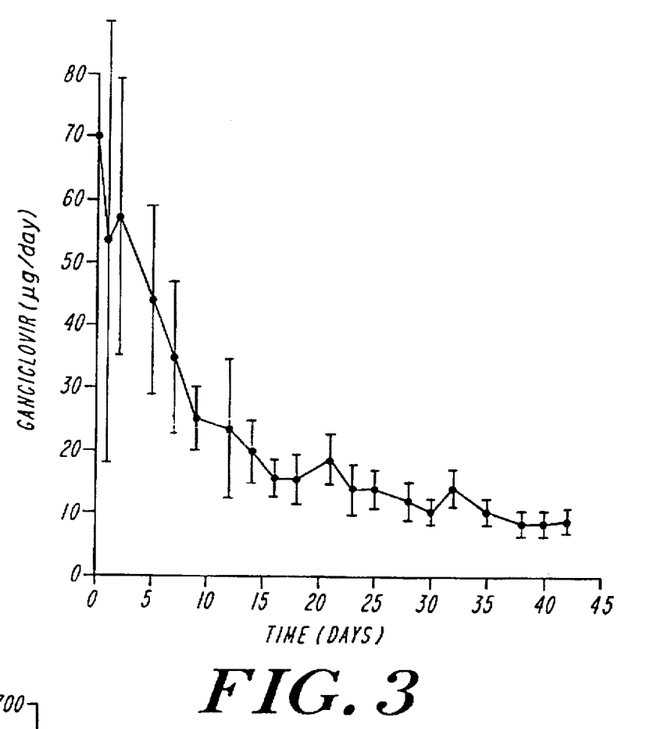
FIG. 3 shows drug release in micrograms/day of microspheres prepared in accordance with the present invention using a biodegradable polymer of relatively low molecular weight.

The drug release rates were faster from microspheres of 0.42 dl/g and 0.39 dl/g PLGA than from the 0.53 dl/g polymer. The ganciclovir loading in the 300–500 μm microspheres was 95% of the theoretical amount, but decreased to 93% in the 212–300 μm microspheres, and 34% in the 106–212 μm microspheres obtained from the same preparation. Ten mg of the 300–500 μm microspheres released ganciclovir at a decreasing rate for at least 42 days, as shown in FIG. 3. At the conclusion of the experiment, the released amount of drug was within 75–80% of the initial load. The amount of drug remaining in the microspheres plus the amount released was equal to the initial load.

Figure 4:
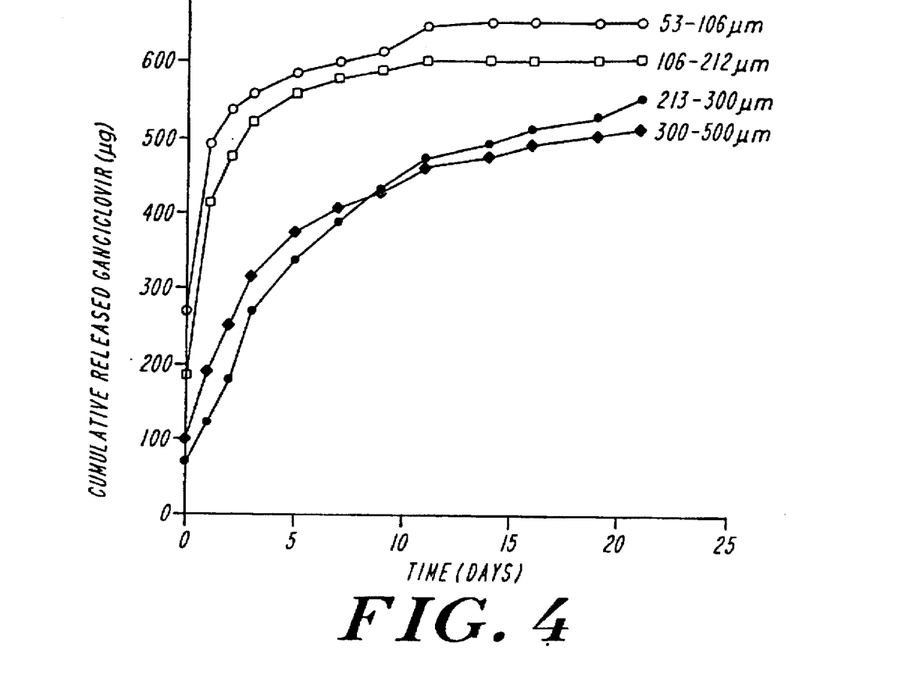
FIG. 4 illustrates cumulative release for the present invention as a function of microsphere size, using a relatively low molecular weight polymer.

For a given microsphere preparation made with 250 mg of the 0.39 dl/g polymer per 25 mg ganciclovir and 100 μl of FSiO, the ganciclovir was released faster from the smaller microspheres that encapsulated less ganciclovir (53–106 μm with 75% of the theoretical ganciclovir; 106–212 , μm with 84% of the theoretical drug) than from the larger microspheres with higher drug loads (212–300 μm with 93% of theoretical ganciclovir; 300–500 μm with 95% of theoretical) (FIG. 4). For all sizes of microsphere, the released drug per day during this time was within the therapeutic range of 0.09–15.57 μg/total vitreous calculated from the ED50 of 0.02–3.48 μg/ml and from the human vitreous volume 4.5 ml.

Figure 5:
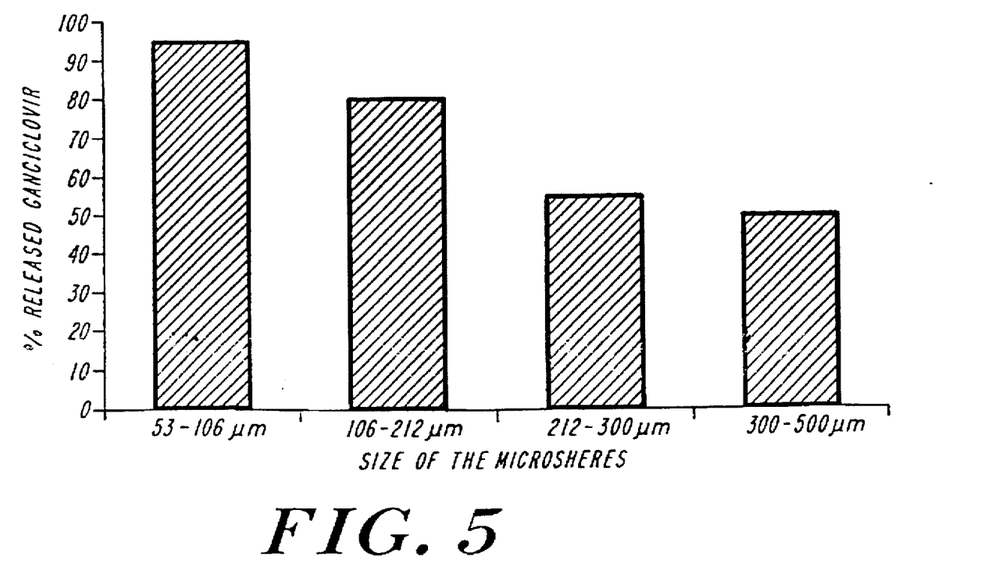
FIG. 5 illustrates percent of drug released by day 14, as a function of microsphere size.

Even including the initial drug burst, concentrations of ganciclovir released from microspheres never reached 100 μg/day. The amount of ganciclovir released at a given time relative to drug load was inversely proportional to the size of the microspheres as shown in FIG. 5.

Figure 6:
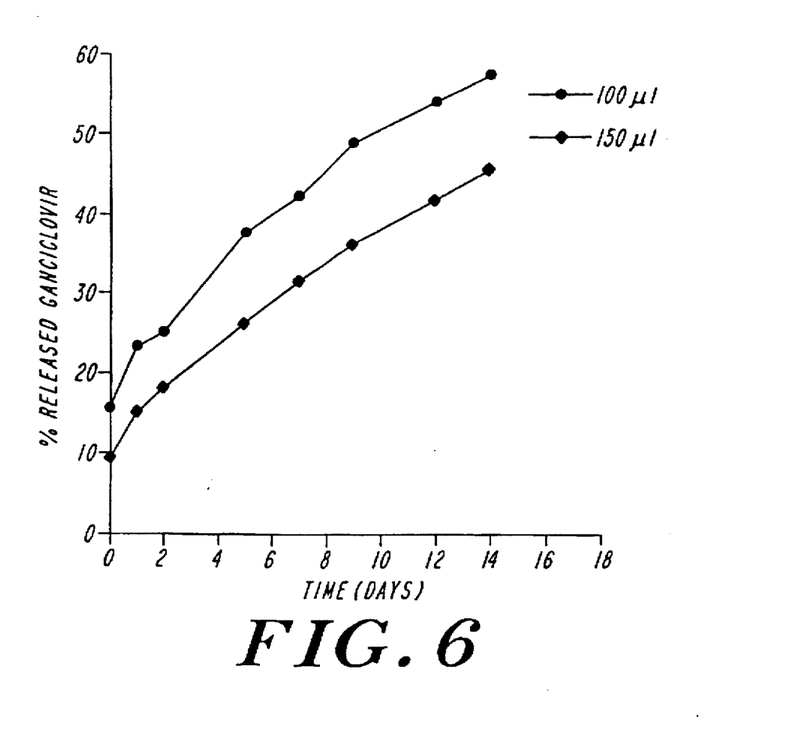
FIG. 6 shows a drug release curve for large microspheres prepared using a degradable polymer.

FIG. 6 shows the results of another experiment performed to observe the influence of FSiO on the ganciclovir release rate. For these experiments, the microspheres were prepared with 0.42 dl/g polymer (250 mg in 0.7 ml acetone) using either 100 μl or 150 μl of FSiO. As shown, the drug was released more slowly from the 300–500 p.1 diameter microspheres prepared with 150 μl of FSiO having a ganciclovir loading of 94.5%) than from the microspheres prepared with 100 μl FSiO having a ganciclovir loading of 92.3%.

Another comparison with the prior art is instructive. Multi-phase polymeric microspheres containing a drug or molecular compound dispersed in a polymeric matrix as described in U.S. Pat. No. 5,288,502 have been prepared by using a water solution of a drug to form a water-in-oil emulsion, in which the water-dissolved drug is protected within oil droplets dispersed in the biodegradable polymeric matrix. In the present invention, by contrast, there is no aqueous carrier; rather, the solid drug is dispersed in oil droplets which are then dispersed in the biodegradable polymeric matrix. The absence of water in the present preparation of microspheres accounts for a markedly higher loading capacity of the drug and a longer release time. The amount of encapsulated drug (expressed in milligrams of drug per gram of microspheres) obtained in the present technique is more than twice the amount cited in U.S. Pat. No. 5,288,502. That is, while the maximum content of drug per gram of microspheres cited in U.S. Pat. No. 5,288,502 is 38.6 mg/g, the present invention attains a loading of 95 mg/g of microspheres, which was achieved with the microspheres having the drug release curve shown in FIG. 3.

Microsphere Morphology

Figure 7A:
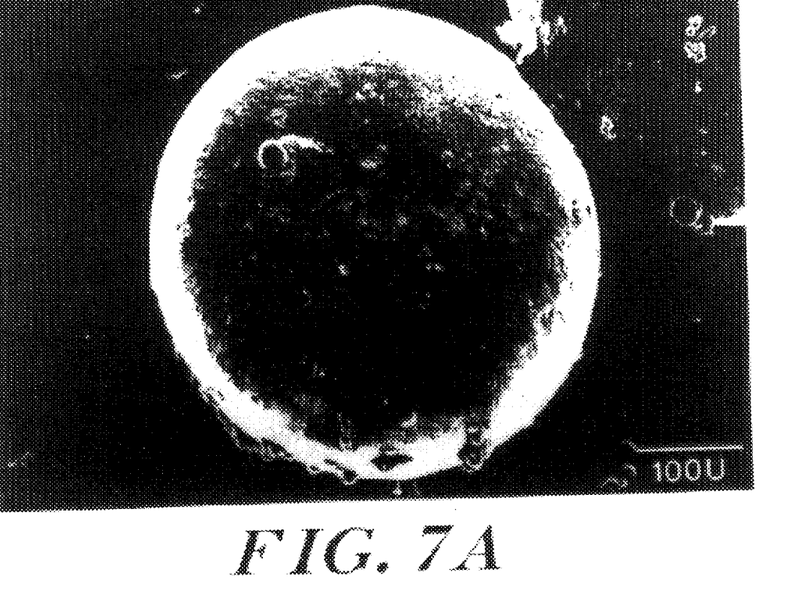
FIG. 7A is an SEMx160 micrograph of a large microsphere prepared with a degradable polymer.

SEM examination of the microspheres prepared in accordance with the present invention from 0.39 dl/g polymer showed different structures at the surface and in the interior. The microspheres were round and nearly homogeneous in shape for each size. The surface of the microspheres was generally smooth, but with some dimples or holes as seen in FIG. 7A. Inside the fractured microspheres, we observed some dark areas that were probably lacunas-little lakes or oil bodies—consisting of the suspension of the powered solid ganciclovir in FSiO, as appears in FIG. 7B. By day 28 of the release experiment, the surface of the microspheres was slightly eroded with surface pitting, as shown in FIG. 8A. At that time, an interior view revealed that the microspheres had become highly porous inside, as appears in FIG. 8B.

Experimental Data

A more detailed understanding of the techniques and variations explored by the inventors may be had from the Figures herein, to which the following specific legends apply.

FIG. 1- Microspheres prepared by technique 1 with 10 mg ganciclovir in 25 μl of distilled water and 500 mg of polymer in 0.5 ml methylene chloride. Release of ganciclovir from 10 mg PLGA (inherent viscosity, 0.65 dl/g ) microspheres of different diameters (53–106 μm loaded with 80 μg ganciclovir; 106–212 μm with 89 μg; and 212–300 μm with 120 μg ganciclovir) in 1.5 ml of 0.01M PBS, pH 7.0.

FIG. 2- Ganciclovir release in 1.5 ml PBS from 10 mg of 0.53 dl/g PLGA microspheres prepared by technique 1 (106–212 μm microspheres with 199 μg ganciclovir, and 212–300 μm with 242 μg) and technique 3 (106–212 μm microspheres with 431 μg ganciclovir and 212–300 μm with 460 μg ganciclovir). By day 25, the 106–212 μm microspheres prepared by technique 1 had released about 90% of the encapsulated drug; the same size microspheres made by technique 3 had delivered less than 50% of their drug load. [T1, technique 1; T3, technique 3.]

FIG. 3- The ganciclovir release rate in 1.5 ml of PBS from 0.39 dl/g PLGA 300–500 μm microspheres (950 μg ganciclovir/10 mg microspheres ) prepared by technique 3 (SiO as external phase, and 25 mg ganciclovir in 100 μl of FSiO dispersed in PLGA in acetone). Data points (±standard deviations) from 9 drug release experiments under the same working conditions.

FIG. 4- Cumulative ganciclovir released in 1.5 ml PBS from 10 mg microspheres of different sizes (53–106 μm: 681 μg ganciclovir; 106–212 μm: 764 μg; 212–300 μm: 845 μg; and 300–500 μm: 864 μg ) prepared by technique 3 with 250 mg of 0.39 dl/g polymer in 0.7 ml acetone, and 25 mg ganciclovir in 100 μl FSiO.

FIG. 5- Percentage of ganciclovir released from the microspheres in FIG. 4, in 1.5 ml PBS by day 14 as a function of microsphere size.

FIG. 6- Release of ganciclovir in 1.5 ml PBS from 10 mg microspheres (300–500 μm diameter) prepared with 250 mg of 0.43 dl/g PLGA and 25 mg ganciclovir by technique 3, with 100 or 150 μl FSiO, respectively.

Figure 7B:
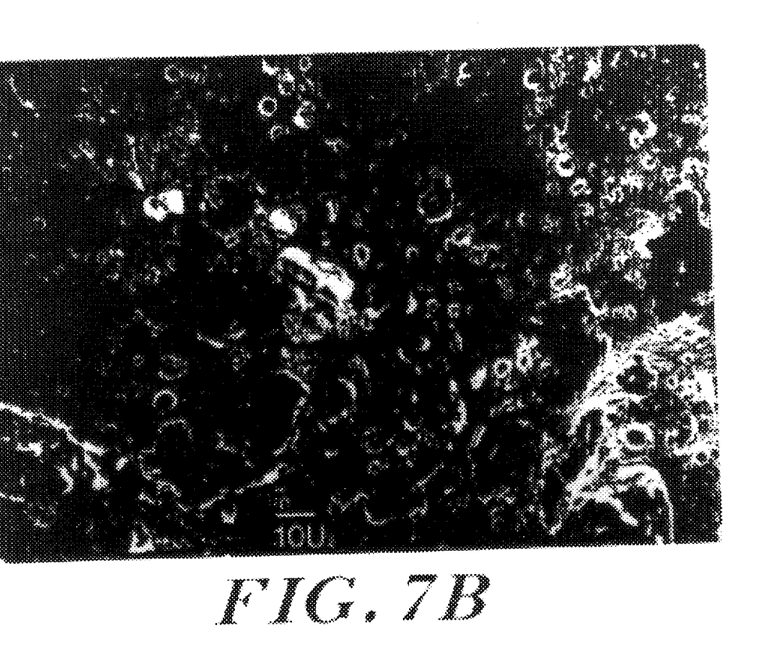
FIG. 7B is a corresponding micrograph of the microsphere interior at greater magnification.
Figure 8A:
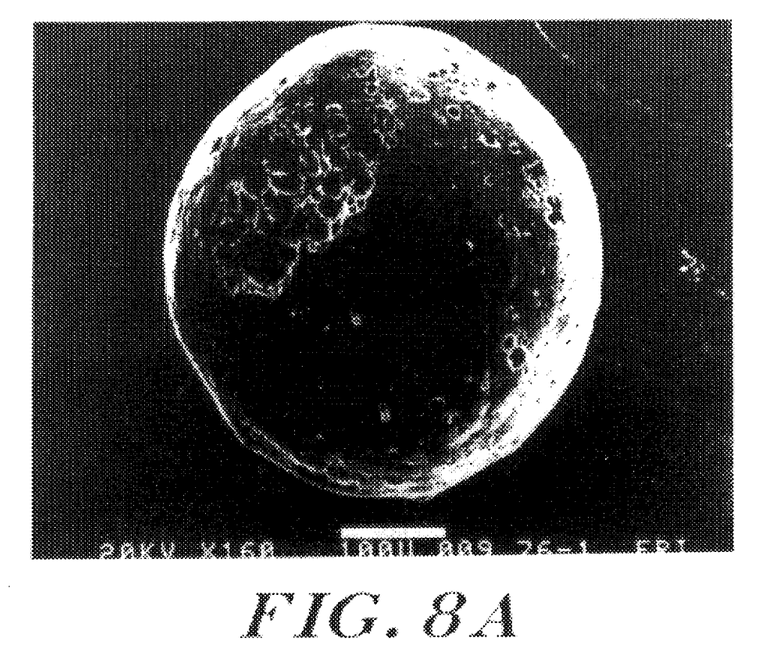
FIG. 8A shows a corresponding SEMx160 view of a microsphere as in FIG. 7A, taken after 28 days of in vitro degradation and release.

FIG. 7- (a) Microspheres (300–500 μm) prepared by technique 3, with 250 mg 0.39 dl/g PLGA, 25 mg ganciclovir and 100 μl FSiO (SEM x160). (b.) Inside view of fragmented microsphere (x600)

Figure 8B:
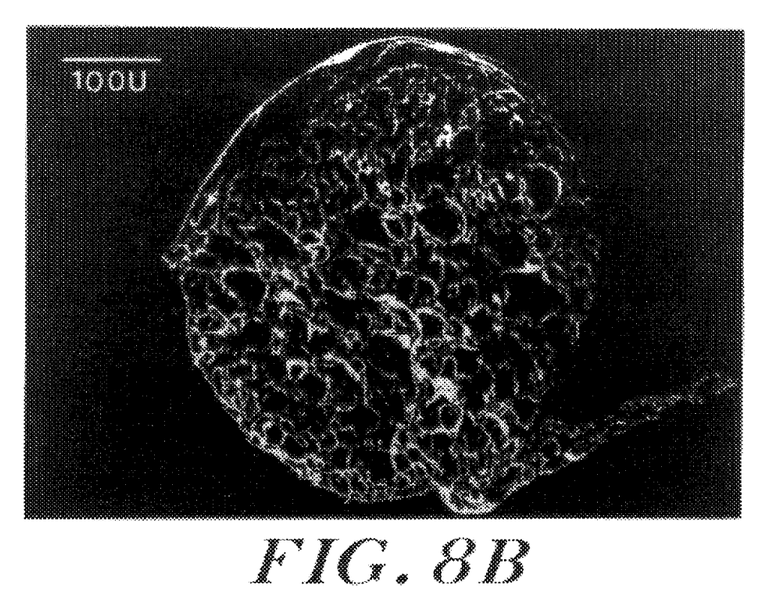
FIG. 8B shows a corresponding view of the interior of the semi-degraded microsphere of FIG. 8A.

FIG. 8.-(a) Microspheres from the same preparation as FIG. 7 after 28 days in vitro ganciclovir release study in PBS (x160). (b). Inner view of a fragmented microsphere observed at the same time as (a) (x160).

Discussion

The standard double-emulsion technique (technique 1) for preparing PLGA microspheres has been reported as allowing good sustained release for hydrophobic drugs such as retinoic acid, and also for proteins. However, for small water-soluble molecules such as ganciclovir, the drug loading in the microspheres is relatively low due to the partition of the drug to the external aqueous phase of the emulsion. Furthermore, the release rate of a hydrophilic drug to an aqueous environment is much faster than for hydrophobic drugs.

When applying this technique to ganciclovir, a large amount of ganciclovir was lost to the aqueous phase during the solidification of the microspheres. As the volume of water used to dissolve the drug in the microsphere preparation was increased, it took longer for the microspheres to solidify and more drug was lost to the aqueous phase. Conversely, by using a higher viscosity polymer and increasing its concentration, the drug loading in the microspheres increased, and the time of solidification decreased.

When the microspheres prepared by technique 1 were immersed in PBS, the water penetrated through the holes in the microspheres, resulting in rapid release of the hydrophilic drug. When the volume of the first inner emulsion was increased, while the other parameters in the preparation were kept constant, the rate of drug release also increased, apparently due to an increasing number of pores in the microspheres. These difficulties caused unfavorable drug release characteristics.

The best results from the prior art technique 1 for ganciclovir loading achieved 60% of theoretical, and for ganciclovir release, best results were obtained with the large microspheres (212–300 μm) of the heaviest, (0.65 dl/g) polymer (FIG. 1). However, the amount of ganciclovir released daily from 10 mg of microspheres, even during the ten initial days of the release study, was too low compared with that obtained from a currently available ganciclovir-releasing implant (1 μg/h). Therefore, technique 1, which yielded well-shaped microspheres, as well as technique 2, which failed to produce a good yield of microspheres, were both deemed unsuitable to economically or effectively prepare ganciclovir loaded PLGA microspheres with a strength and with release characteristics useful for intravitreal treatment of CMV retinitis.

The technique of the present invention (technique 3 described above) when used for preparing ganciclovir-loaded microspheres, required mixing an acetone solution of PLGA with a mixture of powdered ganciclovir in FSiO to obtain a fine dispersion of the drug. This dispersion was further dispersed in a small amount of a solution of 10% acetone in SiO, with a silicone emulsifier DMSiEPO. The SiO does not dissolve the drug, the FSiO, or the polymer, but the acetone is partially soluble in SiO and is volatile. Therefore, when the second dispersion was stirred in a large volume of SiO with 10% acetone, the acetone in the dispersion migrates to the SiO whence it evaporates, yielding the solid microspheres. Thus the SiO serves as a drying agent for the FiSO-polymer system. The solidification of the polymer at the interface with the external phase (in this case SiO) results in an excellent yield of microspheres that contained the entrapped suspension of ganciclovir in FSiO. These microspheres have a smooth surface, visible in the Figures, which may be due to the crystallinity of the polymer and the fact that the interior resulting from the two phase separation, i.e., the accumulation of suspended droplets, is rather spongy. Polymer solidification at the microsphere surface is the first step of microsphere solidification that entraps the bulk of the polymer with the suspended drug in FSiO. The polymer inside the microsphere then precipitates as the acetone solvent diffuses to the outside oil phase and evaporates. The resulting microsphere structure, illustrated in the micrographs, resembles the structure of a pomegranate, with a highly segmented and protected interior.

Most of the SiO in the microspheres is removed by washing in hexane, which does not dissolve the drug, the FSiO, or the polymer. Microspheres prepared using this technique are more hydrophobic than those prepared by technique 1 because of residual SiO and FSiO. Not only a better loading but also a better release profile of ganciclovir were obtained from the microspheres prepared by technique 3 than by the standard double-emulsion technique (technique 1). When the drug release profiles of the microspheres prepared by both techniques were compared, no exotic differences were found between the shapes of release curves obtained (FIG. 2). Nevertheless, considering the amount of encapsulated drug for each technique (42% or 199 μg/10 mg of microspheres for technique 1 and 91% or 431 μg/10 mg of microspheres for technique 3 in the 106 μm particles), by day 25 the 106–212 μm microspheres of technique 1 had released almost 90% of the drug, and those of technique 3 had delivered less than 50% of the drug. This is because the hydrophobic FSiO retards but does not block the access of the drug to the water as it seeps into the porous microspheres.

For the same polymer and preparation technique, the biggest microspheres hydrolyzed more slowly than the smaller ones that had a larger total surface area. In addition, the drug in the inner channels of the bigger microspheres took more time to reach the surface than in the smaller microspheres. Therefore, the best ganciclovir release profiles from microspheres in the sizes and polymers tested were seen with the larger microspheres (having higher drug loading) prepared from the lower inherent viscosity PLGA (which undergoes faster polymer hydrolysis). Ten mg of the 300–500 µm microspheres of 0.39 dl/g PLGA prepared at a polymer/ganciclovir ratio of 250 mg/25 mg and 100 µl FSiO were found to release ganciclovir in vitro at concentrations within therapeutic ranges for at least 42 days, as plotted in FIG. 3. The drug release profile from these microspheres was characterized by an initial ganciclovir burst, followed by a gradual decrease in the rate of release that slowed down after about ten days and continued at a lesser rate for at least one month longer. The drug in the open pores at the surface of the microspheres may be dissolved rapidly in the PBS, and then the PBS migrates through the porous polymer. As the boundaries of the FSiO lacunae are breached, the oil is freed from confinement and may flow in the pores. Upon release of the FSiO from the microspheres, the oil microdroplets contact the aqueous at their surface and the drug suspended in oil dissolves in the aqueous environment, as it reaches the droplet surface. The overall release, governed by polymer degradation and oil/drug diffusion is slow and sustained at a highly uniform rate.

All the in vitro drug release results reported here were obtained for 10 mg dose of drug-loaded microspheres in a 1.5 ml. volume of PBS. Higher amounts of drug can be obtained from increasing amounts of microspheres. Because, the degradation rate of the microspheres in vivo may be greater, the drug release rate in vivo is expected to be faster than in the conditions tested in vitro. However, this must be further investigated.

Overall, a high degree of control over critical delivery parameters of a hydrophilic drug was obtained. The ganciclovir release rate from the microspheres prepared by the new technique is a function of the molecular weight of the polymer, drug loading, amount of FSiO, and the microsphere size. One potential drawback of FSiO in the formulation of PLGA microspheres is that the fluorosilicone oil is nonbiodegradable and remains as a residue after the micro spheres have dissolved. However, the small amount of residual ocular FSiO should not present a tolerance problem for potential intraocular injection of the microspheres in an AIDS patient with CMV retinitis. Intravitreous injections of SiO are often used as internal retinal tamponade in AIDS patients who develop retinal detachment associated with retina necrosis. FSiO has also been used but less frequently than SIO as an intravitreous implant in complicated cases of retinal detachment. Thus, sustained release microspheres of the described preparation protocol appear fully compatible with intravitreal and other localized delivery regimens.

While a FSiO was selected for the in vitro studies, a fully biodegradable oil, such as described in the aforesaid patents, may be used as the drug-loaded inner phase, and the second immiscible oil used in preparing the microspheres may also be biodegradable. Furthermore, the technique of protecting a micropulverized solid hydrophilic agent by suspension in a hydrophobic oil and preparing the microspheres with non-aqueous solvents is broadly applicable to other agents including drugs and biological preparations and fragments of diverse type. The invention is expected to have particular utility for the delivery of agents which require sustained delivery periods, in excess of weeks or months, and which are necessarily available in very limited quantities either because of their cost, their potency, the limited bodily space in which they are to be applied, the difficulty of their preparation or synthesis, or other reason.

The invention being thus described, variations, modifications and adaptations thereof will occur to those skilled in the art, and such variations, modifications and adaptations are considered to be within the spirit and scope of the present invention, as defined in the claims appended hereto.

What is claimed is:

1. A method of preparing microspheres encapsulating a pharmacologically active agent to enable delivery and sustained release of the agent, such method comprising the steps of selecting a biodegradable polymer and a volatile non-aqueous solvent, adding the pharmacologically active agent suspended in a first oil to said polymer and non-aqueous solvent, and mixing them to produce an aqueous-free dispersion in which the drug is contained primarily in said first oil, selecting a second oil which is immiscible with said first oil and in which said solvent is at least partially soluble, mixing said aqueous-free dispersion in a volume of said second oil and solvent with an emulsifier, and drying the solvent therefrom to produce well-formed microspheres, and removing said second oil from said microspheres with a second solvent, said second solvent being insoluble in said polymer and said first oil, wherein said pharmacologically active agent, is a hydrophilic agent and said first oil is selected to substantially hinder dissolution in an aqueous environment, so that release of the agent from microspheres occurs as the polymer degrades releasing said first oil to contact said environment at a surface and said agent diffuses from the surface.

2. The method of claim 1, wherein at least one of said first and second oils is a silicone oil.

3. The method of claim 1 wherein at least said first oil is a fluorosilicone oil.

4. The method of claim 1, wherein at least one of said oils is a biodegradable oil.

5. The method of claim 4, wherein at least one of said oils is an oil selected from the group consisting of sesame oil, castor oil, mineral oil, and tocopherol.

6. The method of claim 1, further comprising the step of grading the microspheres into batches of different size, and selecting a size of microsphere corresponding to duration of a desired release curve.

7. The method of claim 1, wherein the step of selecting a biodegradable polymer includes selecting a copolymer of lactic acid and glycolic acid and the step of adding a pharmacologically active agent suspended in a first oil adds said pharmacologically active agent to the selected copolymer to produce the aqueous-free dispersion.

8. The method of claim 1, wherein said first oil is selected to be insoluble in the second oil, in said solvents, and in water, so that said microspheres form a shell of said polymer enclosing droplets of said first oil containing said pharmacologically active agent, the droplets being separated by a matrix of sheets or shells of said polymer, whereby said pharmacologically active agent is slowly released as the polymer degrades.

9. The method of claim 8, wherein the polymer and first oil are selected to form microspheres of a size selected to achieve a release time of at least two weeks.

10. A method of preparing microspheres for delivering a pharmacologically active agent to the vitreous, such method comprising the steps of mixing a biodegradable hardenable polymer in a non-aqueous solution with a mixture of said agent in a hydrophobic oil to form a non-aqueous two-phase dispersion containing said agent 
stabilizing the dispersion of said non-aqueous two-phase dispersion with an emulsifier in a second oil that is immiscible with the first oil to form microspheres of said polymer enclosing a multi-chambered interior defined by precipitated dividing walls formed of said polymer with inclusions of said hydrophobic oil carrying said agent, the step of stabilizing including drying said non-aqueous solution in said second oil, and washing said second oil from said microspheres to produce well-formed spheres with complex porosity that biodegrade to release said agent at a therapeutic rate.

11. A method of ocular treatment, such method comprising the steps of preparing microspheres of an agent suspended in a hydrophobic oil, said oil being held as lacunae within foliations and shells of a hardenable biodegradable polymer, each microsphere being enclosed by a substantially spherical outer shell of said polymer drying said microspheres in an oil which is immiscible with said hydrophobic oil to remove solvent therefrom for a period effective to harden said foliations and shells as well as said outer shell, and selecting a quantity of said microspheres having a total volume less than one milliliter and having a diameter greater than approximately several hundred micrometers effective to release said agent at a rate above a minimum therapeutic rate for over one month.

12. The method of claim 11, wherein the agent is a hydrophilic preparation of an agent selected from the group consisting of ganciclovir and foscarnet.

13. The method of claim 12, wherein the microspheres have a selected diameter which is between fifty and five hundred micrometers, and said therapeutic rate is over approximately five micrograms per day.

14. A therapeutic preparation comprising microspheres of a bioactive agent suspended in an oil, wherein an outer shell of a hardened biodegradable polymer encloses and defines each microsphere, said oil being a hydrophobic oil enclosed within said outer shell as lacunae between sheets and shells of said hardened biodegradable polymer, the microspheres being between approximately 300–500 μm in diameter and compounded with said agent suspended as a powder in said oil, and said microsphere being dried in a second oil which is immiscible with the hydrophobic oil so that substantially all of said agent remains in said hydrophobic oil and the microspheres are effective to release said agent for an extended period at a therapeutic rate to an aqueous environment as said polymer degrades.

15. The method of claim 1, wherein at least one of said oils is selected from among the group consisting of biocompatible oils and bioactive oils.

16. The method of claim 11, wherein the agent is selected from among the group consisting of hydrophilic preparations of proteins and hydrophilic preparations of antiviral agents.

17. The method of claim 1, wherein said first oil is a biodegradable oil.

18. The method of claim 17, wherein said biodegradable oil is an α-tocopherol.

* * * * *

UNITED STATES PATENT AND TRADEMARK OFFICE
CERTIFICATE OF CORRECTION

PATENT NO. : 5,718,922
DATED : February 17, 1998
INVENTOR(S) : Herrero-Vanrell, R. et al.

It is certified that error appears in the above-identified patent and that said Letters Patent is hereby corrected as shown below:

Column 1,
Line 4, the following two sentences should be inserted:
-- STATEMENT OF RIGHTS
This invention was made with government support under Grant EY 00327 awarded by the National Institutes of Health. The Government has certain rights in the invention. --

Signed and Sealed this

Twenty-first Day of October, 2003

JAMES E. ROGAN
*Director of the United States Patent and Trademark Office*